United States Patent [19]

Matsuo et al.

[11] 4,308,350

[45] Dec. 29, 1981

[54] METHOD FOR PRODUCING CACAO BUTTER SUBSTITUTE

[75] Inventors: Takahal Matsuo, Sennan; Masahiko Terashima, Osaka; Yukio Hasimoto, Kishiwada; Wataru Hasida, Osaka, all of Japan

[73] Assignee: Fuji Oil Company, Limited, Osaka, Japan

[21] Appl. No.: 897,771

[22] Filed: Apr. 19, 1978

[30] Foreign Application Priority Data

Apr. 28, 1977 [JP] Japan .................................. 52-49678

[51] Int. Cl.$^3$ ............................ C12P 7/64; A23D 5/02
[52] U.S. Cl. ..................................... 435/134; 435/911; 435/921; 435/938; 435/944; 426/33
[58] Field of Search ............................. 195/30, 82, 83; 435/134

[56] References Cited

U.S. PATENT DOCUMENTS 4,032,405  6/1977  Tatsumi et al. ........................ 195/82

*Primary Examiner*—Lionel M. Shapiro
*Attorney, Agent, or Firm*—Wenderoth, Lind & Ponack

[57] ABSTRACT

Improved method for producing fats and oils rich in 1,3-disaturated-2-unsaturated-triglycerides (e.g. 1,3-distearyl-2-oleyl compound and 1-palmityl-2-oleyl-3-stearyl compound) useful as a cacao butter substitute, which comprises cultivating a microorganism being capable of assimilating a higher alkyl derivative and producing fats and oils containing 1,3-disaturated-2-unsaturated-triglycerides in a specific medium containing a mixed carbon source comprising at least one stearyl compound and at least one of other carbon compounds selected from a palmityl compound, an oleyl compound and a saccharide under an aerobic condition, collecting the cells of the microorganism and recovering the fats and oils from the cells.

9 Claims, 1 Drawing Figure

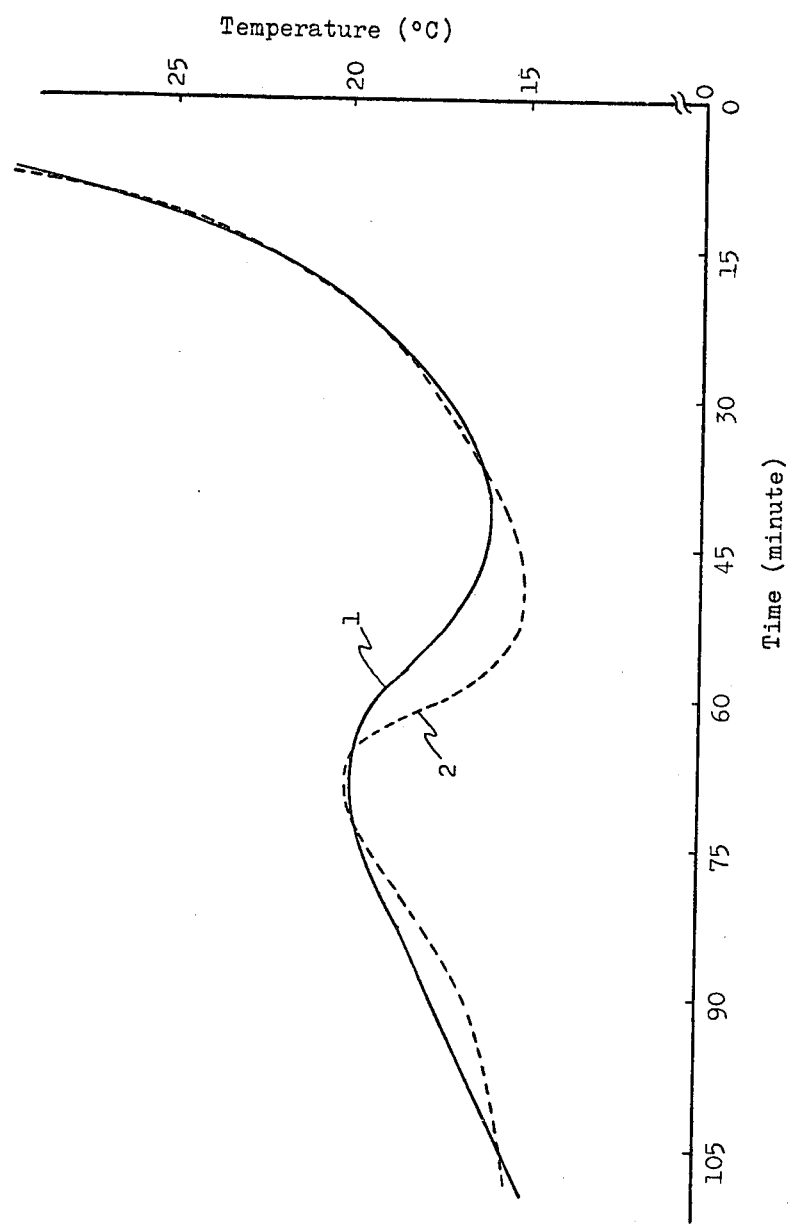

METHOD FOR PRODUCING CACAO BUTTER SUBSTITUTE

The present invention relates to a method for producing fats and oils by using microorganisms. More particularly, it relates to a method for producing a cacao butter substitute which is usually called "hard butter" or "hard fat" by cultivating a microorganism and collecting the fats and oils accumulated in the cells thereof.

It is well known that a chocolate is one of the important materials for confectionery and that the chocolate has such unique characteristics that it is solid at room temperature but when it is kept in the mouth, it melts, which characteristics are owing to the specific glycerides components of cacao butter contained in the chocolate. The cacao butter contains a large amount of 1,3-disaturated-2-unsaturated-triglycerides (hereinafter, referred to as "SUS"), for instance, 24.2% by weight of 1,3-distearyl-2-oleyl compound, 32.8% by weight of 1-palmityl-2-oleyl-3-stearyl compound and 12.1% by weight of 1,3-dipalmityl-2-oleyl compound [cf. J. Sampuguna et al, Lipids, Vol. 4, page 444 (1969)]. However, the cacao butter is harvested from nature and is very expensive. Furthermore, the cacao butter ($\beta$ type) has a fixed melting point, 34°-35° C., but on the other hand, the suitable melting properties of chocolate vary with the season, region, or the like, and hence, it is difficult to give the cacao butter the most suitable melting properties adaptable to the individual chocolate. Accordingly, there have been proposed various cacao butter substitutes having similar melting properties to those of the natural cacao butter. A first cacao butter substitute is SUS-rich fats and oils, such as vegetable butters (e.g. shea butter, illipe butter, Borneo tallow, phulwara butter, or kokum butter) or palm oil, which may be used as it is or after being fractionated, and a second one is the product obtained by hydrogenating a liquid oil (e.g. soybean oil) and, if desired, followed by the fractionation thereof.

According to the first one, the substitute can be admixed with the cacao butter in any optional ratio to give an excellent product (subject to the high content of the SUS component), because the substitute has macroscopically similar glyceride components to those of the cacao butter. However, since this substitute is also harvested from nature, there is the same problem as with the cacao butter. Particularly, the commercially used starting materials for the vegetable butter, *Butyrosperumum parkii* (the starting plant for shea butter) and *Madhuca longifolia* (the starting plant for illipe butter), are a wild plant, and it is very difficult to get the starting materials because the harvest thereof depends on the harvest of the fruits and further because of the recent instability of the political situation and nationalism in the producing countries in the torrid zone.

According to the second one, the starting materials of soy bean oil etc. can easily be obtained because they are produced in various countries in the world. However, this substitute can hardly be admixed in a large amount with the cacao butter because the glyceride components of the substitute are significantly different from those of the cacao butter. Accordingly, when this substitute is used, there can not be obtained the desired chocolate having the excellent melting properties as the product produced by using natural cacao butter but the product is a mere imitation flavored with cacao bitters, and hence, this substitute is rather not a true cacao butter substitute.

Under the circumstances, it is desired to get more easily an excellent cacao butter substitute having glyceride components similar to those of the natural cacao butter without relying on the wild plants in the torrid zone. Aiming at the solution of this problem, the present inventors have conducted studies on a method for producing the desired cacao butter substitute by a fermentation process.

The fermentation process has been remarkably developed in various fields, such as the production of antibiotics, enzymes, amino acids, proteins, or the like, but has not yet been industrially developed in the field of fats and oils, notwithstanding it is well known that various microorganisms such as fungi, bacteria, yeasts or algae can accumulate fats and oils as the metabolite in their cells in such large amounts as 50 to 60% by weight, occasionally about 80% by weight. The reason why the fermentation process has not yet been applied to the industrial production of fats and oils may be mainly that the fermentation process is very expensive and the product can not compete with the commercially available, animal and vegetable fats and oils in price.

As the results of the extensive studies by the present inventors, it has already been found that various microorganisms could produce SUS-rich fats and oils which have similar components to those of the natural cacao butter and hence are useful as a cacao butter substitute (cf. U.S. Pat. No. 4,032,405 and Japanese patent appln. No. 39918/1976).

Although these microorganisms can accumulate a large amount of the fats and oils having similar components to those of the natural cacao butter, the present inventors have further studied to improve the accumulation amount and the components of the produced fats and oils, so that the fermentation process can be employed for the more economical production of the desired cacao butter substitute on an industrial scale. As a result, it has now been found that when the microorganisms are cultivated in a specific medium containing a mixed carbon source comprising at least one stearyl compound and at least one of other carbon compounds selected from a palmityl compound, an oleyl compound and a saccharide, the desired fats and oils having excellent glyceride components can be accumulated in a very large amount in the cells.

An object of the present invention is to provide an improved method for producing a cacao butter substitute by a fermentation process.

Another object of this invention is to provide an improvement in the accumulation of fats and oils having excellent triglyceride components similar to those of natural cacao butter in the cells of a microorganism which is cultivated in a medium.

A further object of this invention is to provide an improved method for cultivating a microorganism in a specific medium in order to produce the desired fats and oils in a large amount.

These and other objects of this invention will be apparent from the following description.

According to the present invention, the desired SUS-rich fats and oils can be produced by cultivating a microorganism being capable of assimilating a higher alkyl derivative and producing SUS-containing fats and oils in a specific medium containing a mixed carbon source comprising at least one stearyl compound and at least one of other carbon compounds selected from a palmityl compound, an oleyl compound and a saccharide under an aerobic condition, collecting the resulting cells of the microorganism and then recovering the fats and oils from the cells.

The microorganisms being capable of assimilating a higher alkyl derivative and producing SUS-containing fats and oils include various microorganisms of the genus Candida, Torulopsis, Trichosporon, Pichia and Sporobolomyces, for instance, *Candida guilliermondii* IFO 0838, *Candida guilliermondii* IFO 0566, *Candida tropicalis* OUT 6019, *Candida albicans* OUT 6266, *Candida lipolytica* OUT 6337, Candida sp. ATCC 20503 (FERM-P No. 3900), Candida sp. ATCC 20504 (FERM-P No. 3901), *Trichosporon pullulans* OUT 6260, Trichosporon sp. ATCC 20505 (FERM-P No. 3902), Trichosporon sp. ATCC 20506 (FERM-P No. 3903), *Torulopsis candida* OUT 6186, *Torulopsis etchellsii* OUT 6322, *Torulopsis xylinus* A OUT 6205, *Torulopsis versatilis* OUT 6204, Torulopsis sp. ATCC 20507 (FERM-P No. 3904), *Pichia farinosa* OUT 6121, *Sporobolomyces pararoseus* OUT 6145, or the like. The microorganisms are cultivated in a specific medium containing a mixed carbon source under an aerobic condition to accumulate a large amount of fats and oils having similar components to those of cacao butter in the cells, from which the SUS-rich fats and oils having excellent properties suitable for cacao butter substitute are obtained, if desired, followed by fractionation thereof.

For instance, when Torulopsis sp. ATCC 20507 (FERM-P No. 3904) is cultivated in a medium containing a mixed carbon source comprising methyl stearate, methyl palmitate and glucose, fats and oils having the following fatty acids components can be obtained from the cells:

| $C_{14}$ | $C_{16}$ | $C_{16-18}$ | $C_{18}$ | $C_{18:1}$ | $C_{18:2}$ | $C_{20}$ | $C_{18:1}$ |
|---|---|---|---|---|---|---|---|
| 0.2 | 21.2 | 3.2 | 35.2 | 36.0 | 3.9 | 0.2 | 0.1 |

Analysis of the triglyceride components of the fats and oils by a pancreatic-lipase method (cf. J. Amer. Oil Chem. Soc., Vol. 41, pages 693–696) shows that they contain 6.2% by weight of 2-unsaturated-1,3-dipalmityl compound, 22.5% by weight of 1-palmityl-2-unsaturated-3-stearyl compound and 20.5% by weight of 2-unsaturated-1,3-distearyl compound (SUS: 49.2% by weight in total) and further 12.8% by weight of other tri-saturated compounds, 27.5% by weight of diunsaturated compounds and 6.9% by weight of 1- or 3-monounsaturated compounds. From this fact, it is clear that the fats and oils thus obtained can be used as a cacao butter substitute even as they stand, and further, when they are fractionated for one time to remove the components having a lower melting point, an excellent cacao butter substitute can be obtained.

In addition to the strains listed hereinbefore, other microorganisms suitable for the present invention can be isolated from leaves and stems of vegetables and surface parts of other plants. Among the microorganisms belonging to the above-mentioned genus, the suitable microorganisms can be elected by checking experimentally the ability of producing SUS-rich fats and oils. The check of the ability is conveniently carried out by screening previously the microorganisms which can produce fats and oils containing a large amount of $C_{16}$ and $C_{18}$ saturated fatty acids and $C_{18:1}$ fatty acids by using gas chromatography. However, this screening is a mere supplemental means because $C_{18:3}$ fatty acid is not necessarily 2-unsaturated fatty acid but includes other unsaturated fatty acids. From the standpoint of industrial practice, it is preferable to elect the microorganism which can produce fats and oils in the range of content of fats and oils in the cells: 30% by weight or more; yield of fats and oils per consumed carbon source: 10% or higher; and SUS content in fats and oils in the cells: 30% by weight or more. The microorganisms may also include various mutants thereof obtained by conventional mutation, such as irradiation with X-ray, γ-ray or other radiations, nitrogen mustards, treatment with antimetabolites, or the like in order to improve the ability.

In practice of the present invention, the pure culture of a strain being capable of assimilating a higher alkyl derivative and producing SUS-containing fats and oils is inoculated into the medium containing a mixed carbon source and cultured under an aerobic condition at a temperature suitable for the growth of the microorganism. Since the microorganisms are aerobic, shake culture is more preferable than stationary culture, and on an industrial scale, the culture in liquid with aeration is preferable.

The medium used in the present invention should contain a mixed carbon source comprising at least one stearyl compound and at least one of other carbon compounds selected from the group consisting of a palmityl compound, an oleyl compound and a saccharide.

Generally, a microorganism takes a carbon source contained in a medium in the cells and decomposes the carbon source to lower molecular weight substances by the aid of an enzyme secreted in the cells. A part of the lower molecular weight substances is consumed as energy for growth of the microorganism and the remainder is polymerized in the cells and is converted into fats and oils, proteins or the like, via intermediates of fatty acids and amino acids, which are accumulated in the cells. Besides, in regard to the production of fats and oils by microorganisms, it is said that in the course of decomposition of the carbon source, a part of the intermediate fatty acids is directly converted into fats and oils without further decomposition.

According to the present invention, the desired cacao butter substitute is produced in the above mechanism of production of fats and oils. Cacao butter contains a large amount of stearic acid as the fatty acid component, and hence, it is preferable to use a medium containing substances which can be converted into stearic acid as the carbon source.

In the course of decomposition of such a carbon source by the microorganism of the present invention, the terminal or comparatively weak bond parts of the substance are attacked by the enzyme and are oxidized or hydrolyzed to form fatty acids. A part of the fatty acids is further affected by the enzyme and thereby the bond of the main chain is oxidized to be converted into an unsaturated bond and then is converted into a lower molecular weight compound, or is converted into a lower molecular weight compound without conversion to an unsaturated compound.

The present inventors have intensively studied the carbon sources from which fatty acids are produced as the intermediate, and as the result, it has been found that the fatty acid components of the produced fats and oils vary depending on the relationship between the bonding energy at the part of the main chain affected by the enzyme in the course of the formation of fatty acids and the bonding energy at the part of the formed fatty acids affected by the enzyme, while it also depends on the kinds of the microorganism and the culture conditions thereof, because the secreted enzyme varies in the kind and the amount. For instance, in case of the decomposition steps by enzyme: [carbon source]→[saturated fatty acids]→[unsaturated fatty acids]→[lower molecular weight compounds], when the decomposition speed in the first step ([carbon source]→[saturated fatty acids]) is higher than the speed in each subsequent step, the decomposed substances will be contained in the cells almost in the form of saturated fatty acids, and hence, the fats and oils produced in the cells will almost entirely be formed from the saturated fatty acids.

Taking into consideration the above fact, the present inventors have studied on various carbon sources which can produce stearic acid as the intermediate and have found that stearyl compounds such as an alkyl stearate having 1 to 4 carbon atoms in the alkyl moiety (e.g. methyl stearate, ethyl stearate, n-butyl stearate), vinyl stearate, stearyl acetate, stearyl alcohol, stearyl chloride and ammonium stearate are suitable.

When these stearyl compounds are used as a carbon source, the microorganisms can accumulate fats and oils having a high stearyl content, but the fats and oils do not necessarily have similar fatty acids arrangement in the triglycerides to that of cacao butter. When fats and oils have a high stearyl content in the fatty acids components, they have a higher melting point than that of fats and oils having a high content of unsaturated fatty acids. When a microorganism accumulates such fats and oils having a high melting point in the cells thereof, the microorganism will secrete certain substances, so that the conditions are suitable for the accumulation of the fats and oils, but on the other hand, the microorganism has inferior assimilation of the carbon source, and hence, the accumulation of fats and oils are decreased. Moreover, even when a stearyl compound is used as a carbon source, there are occasionally obtained fats and oils having an extremely high unsaturated fatty acid content which are not suitable as a cacao butter substitute, either. These phenomena may be due to the adaptability of the microorganism to the growth circumstance, and the productivity and accumulation of fats and oils may be affected by the circumstance including the specific carbon source. Thus, it is very difficult to settle the most suitable conditions for producing the desired cacao butter substitute.

As the result of the present inventors' further intensive study, it has been found that when at least one other carbon source being more easily assimilated by the microorganism is used together with the abovementioned stearyl compound, the desired fats and oils suitable as a cacao butter substitute can stably be produced by cultivation of a microorganism. Suitable other carbon sources are selected from the group consisting of a palmityl compound, an oleyl compound and a saccharide. Suitable examples of the palmityl compound include methyl palmitate, ethyl palmitate, butyl palmitate, vinyl palmitate, palmityl acetate, palmityl alcohol, and palmityl chloride. Suitable examples of the oleyl compound include oleic acid, methyl oleate, ethyl oleate, butyl oleate, vinyl oleate, oleyl acetate, oleyl alcohol, and oleyl chloride. The saccharide includes monosaccharides (e.g. arabinose, xylose, ribose, glucose, galactose, mannose, etc.), oligosaccharides (e.g. lactose, sucrose, maltose, etc.) and water-soluble polysaccharides (e.g. starch, dextran, etc.). These other carbon sources may be used alone or in a combination of two or more thereof together with one or more stearyl compounds.

The stearyl compound is contained in the medium in the range of 10 to 95% by weight, preferably 25 to 85% by weight, on the basis of total weight of the carbon sources, and the remainder, i.e. 5 to 90% by weight, preferably 15 to 75% by weight, is other carbon sources. When the stearyl compound is used over 95% by weight, there is hardly obtained the desired fats and oils having well balanced fatty acids components suitable as a cacao butter substitute. On the other hand, when the stearyl compound is used in less than 10% by weight, there can not be obtained the fats and oils having desirably high stearic acid content.

In addition to the above mixed carbon source, the medium used in the present invention contains assimilable nitrogen sources (e.g. ammonium sulfate, ammonium chloride, sodium nitrate, urea, corn steep liquor, soy bean powder, peptone, meat extract, yeast extract), essential inorganic salts of potassium, sodium, calcium, magnesium, iron, zinc, phosphor, manganese, copper, or the like (e.g. sodium chloride, potassium chloride, potassium dihydrogen phosphate, magnesium sulfate, ferric sulfate, ferric chloride, zinc sulfate, calcium chloride, manganese chloride, cupric chloride), and further, optionally a slight amount of organic stimulants, such as vitamins (e.g. vitamin $B_1$, vitamin $B_2$), amino acids, or the like.

It is not clear how the microorganism assimilates the stearyl compound and other carbon sources, but it may be assumed that the microorganism will firstly assimilate somewhat other carbon sources and thereafter assimilate the stearyl compound, and thereby, the stearic acid having a high melting point can be utilized for the production of fats and oils.

The above-mentioned nutrient sources are incorporated into the medium in the range suitable for the growth of the microorganism. Suitable range of the nutrient sources may vary depending on the kinds of microorganism, but is usually in the range of C: 0.8-5.0% by weight, N: 0.006-0.17% on the basis of total weight of the medium. The C/N ratio is very important for the growth of the microorganism and hence should be strictly determined by experiment. Decrease of the C/N ratio due to decrease of C content induces significant decrease of production of fats and oils and also the SUS content thereof. In an ideal C/N ratio, not only the amount of the produced cells of the microorganism but also the production amount of fats and oils and also SUS content are increased.

The microorganisms used in the present invention grow at a temperature of 25° to 45° C., preferably 30° to 37° C. Within the preferable temperature range, the higher the cultivation temperature, the larger the content of saturated glycerides in fats and oils produced in the cells. Accordingly, it is favorable to cultivate the microorganism at as high temperature as possible within the above preferable temperature range in order to increase SUS content. The high cultivation temperature is also favorable for industrial continuation fermentation process in view of easier control of the fermentation heat.

The cultivation period of time is usually within 72 hours. Longer cultivation time, such as 96 hours or longer, is not suitable because not only is it uneconomical, but also the saturated fatty acids contained in the produced fats and oils are unfavorably converted into unsaturated fatty acids by the action of the enzyme.

The fats and oils produced in the cells are isolated therefrom as follows. Firstly, the culture broth is filtered or centrifuged to collect the wet cells, in which the culture broth is preferably made acidic in order to make the filtration easier. The wet cells thus collected are ground with colloid mill or ball mill and then extracted with a solvent such as hexane. Alternatively, the wet cells are lyophilized or spray-dried, and then, the fats and oils are taken out from the cells by pressing out with a cage press or expeller or extracting with a solvent such as hexane or by a combination of the pressing and extraction. Alternatively, the wet cells are lyophilized to destroy the cell membrane and returned to room temperature and then extracted with a solvent. Moreover, in order to make the extraction easier, there may be used any other supplemental means, such as destruction of cells with ultrasonic waves, removal of cell membrane by the treatment with hemicellulase, or the like. In experimental scale, it is preferable to grind the wet cells with siliceous sand or glass pellets in a mortar. The cells thus defatted are useful as feedstuffs for animals because they are rich in proteins, vitamins and coenzymes, and further, are useful as a protein source of foodstuffs for humans or as a starting material for nutrient medicines by extracting the protein. The crude fats and oils thus isolated usually contain various impurities, such as mono- and di-glycerides, free fatty acids, phytosterols, phospholipids, carotenoids, or the like, and hence, are subjected to the conventional purification processes, such as deacidification, decoloring and deodorizing.

The purified fats and oils thus obtained can be used as a cacao butter substitute as they stand, but preferably after fractionation thereof in order to increase SUS content. Fractionation method includes a wintering method comprising merely cooling the fats and oils to separate into solid fraction and liquid fraction: a wet wintering method comprising dispersing the fats and oils into an aqueous solution of a surfactant and then cooling the dispersion to separate into crystalline (solid) fraction, liquid fraction and aqueous fraction; and a solvent fractionation method comprising dissolving the fats and oils in an organic solvent and then cooling stepwise to separate into fractions having various melting points. The most suitable method is the solvent fractionation method, because the desired fraction containing a large amount of SUS can easily be obtained by selecting appropriately the kind and amount of the solvent. The solvent fractionation method is usually carried out by three steps: firstly, removal by precipitation of tri-saturated glycerides having a high melting point which cause difficulty of tempering of chocolate because of increase of the viscosity thereof by incorporation of a large amount thereof; secondly, collection by precipitation of the desired di-saturated-mono-unsaturated glycerides; and finally, taking out mono-saturated-di-unsaturated and tri-unsaturated glycerides as a liquid fraction. If the content of the tri-saturated glycerides is small, the first step may be omitted. This fractionation may optionally be carried out before the deodorizing step. Suitable solvents used for the solvent fractionation method include any solvent usually used for fractionation of fats and oils, such as hexane, methyl ethyl ketone, acetone, ethanol, or the like. The fats and oils suitable as a cacao butter substitute have an SUS content of not less than 15% by weight, preferably not less than 25% by weight.

The present invention is illustrated by the following Examples, but is not limited thereto.

EXAMPLE 1

A 150 liter fermentor provided with a stirrer and an aeration duct was charged with a semi-synthetic medium (100 liters) as mentioned below and thereto is inoculated a pure culture (1 liter) of Candida sp. ATCC 20504 (FERM-P No. 3901), *Candida guilliermondii* IFO 0838, *Candida tropicalis* OUT 6019, Trichosporon sp. ATCC 20505 (FERM-P No. 3902), Trichosporon sp. ATCC 20506 (FERM-P No. 3903) and *Torulopsis versatilis* OUT 6204, and each was cultivated under the conditions of aeration volume: 1 V.V.M., rate of stirring: 300 r.p.m., cultivation temperature: 35° C. and cultivation time: 28 hours.

| Medium: | | |
|---|---|---|
| Methyl stearate | 14 | g |
| Methylpalmitate | 6 | g |
| $KH_2PO_4$ | 5 | g |
| $MgSO_4 \cdot 7H_2O$ | 1 | g |
| NaCl | 0.1 | g |
| Yeast extract | 3 | g |
| Water | 1 | liter |
| pH value: 6.0 | | |

(After adjusting the pH value, it was sterilized by heating at 120° C. for 15 minutes)

After the cultivation, the cells were collected by centrifuging the culture broth, spray-dried and then weighed. The cells were pressed in a cage under a static pressure of 110 kg/cm² to separate fats and oils therefrom. The residue was extracted twice with 5-fold amount of n-hexane, and the extract was separated and distilled off to remove the solvent. The residual fats and oils were combined with those obtained above by pressing and the mixture was weighed. Thereafter, the iodine value, acid value, fatty acid components and triglyceride arrangement of the fats and oils were measured. The results are shown in the following Table 1.

TABLE 1

| | Microorganisms | | | | | |
|---|---|---|---|---|---|---|
| | Candida guilliermondii IFO 0838 | Candida sp. ATCC 20504 | Candida tropicalis OUT 6019 | Trichosporon sp. ATCC 20505 | Trichosporon sp. ATCC 20506 | Torulopsis versatilis OUT 6204 |
| Yield of cells (kg) | 0.87 | 0.85 | 1.09 | 0.72 | 1.55 | 0.98 |
| Yield of fats and oils (kg) | 0.31 | 0.30 | 0.31 | 0.46 | 0.94 | 0.33 |
| Content of fats and oils in cells (%) | 34.6 | 35.0 | 28.6 | 64.5 | 60.8 | 34.1 |
| Yield of fats and oils (per consumed carbon source) (%) | 40.3 | 21.0 | 20.6 | 32.5 | 50.9 | 43.7 |
| Iodine value | 46.0 | 45.9 | 46.0 | 40.6 | 40.7 | 39.8 |

TABLE 1-continued

| | Microorganisms | | | | | |
|---|---|---|---|---|---|---|
| | Candida guillier-mondii IFO 0838 | Candida sp. ATCC 20504 | Candida tropicalis OUT 6019 | Trichosporon sp. ATCC 20505 | Trichosporon sp. ATCC 20506 | Torulopsis versatilis OUT 6204 |
| Acid value | 5.8 | 9.0 | 11.3 | 1.3 | 4.6 | 10.5 |
| Fatty acids components (%) | | | | | | |
| $C_{14:0}$ | 0.1 | 0.2 | 1.2 | 0.9 | 1.0 | 2.5 |
| $C_{16:0}$ | 26.0 | 17.6 | 35.2 | 38.6 | 32.4 | 39.1 |
| $C_{16:0}-C_{18:0}$ | 4.3 | 4.7 | 8.7 | 5.2 | 4.2 | 9.9 |
| $C_{18:0}$ | 26.2 | 30.0 | 17.0 | 18.4 | 28.5 | 18.6 |
| $C_{18:1}$ | 38.8 | 46.3 | 31.7 | 31.6 | 25.2 | 23.3 |
| $C_{18:2}$ | 4.6 | 0.8 | 6.0 | 5.2 | 8.3 | 6.3 |
| $C_{18:3}$ | — | 0.1 | 0.2 | — | 0.1 | — |
| $C_{20:0}$ | — | 0.3 | 0.1 | 0.1 | 0.3 | — |
| Triglycerides arrangement (%) | | | | | | |
| Tri-saturat. glycerides | 7.6 | 2.8 | 13.0 | 18.3 | 19.0 | 14.7 |
| Di-saturat. glycerides | | | | | | |
| 2-saturated | 6.2 | 2.1 | 10.7 | 11.5 | 9.8 | 9.0 |
| 2-unsaturated | 42.8 | 50.1 | 37.1 | 39.7 | 44.2 | 41.5 |
| Di-unsaturat. glycerides | | | | | | |
| 2-saturated | 1.2 | 0.4 | 2.2 | 1.8 | 1.3 | 1.9 |
| 2-unsaturated | 35.0 | 37.6 | 30.6 | 24.8 | 22.8 | 28.6 |
| Tri-unsaturat. glycerides | 7.2 | 7.0 | 6.3 | 3.9 | 2.9 | 4.3 |

EXAMPLE 2

A 150 liter fermentor provided with a stirrer and aeration duct was charged with a semi-synthetic medium (pH: 6.0, 100 liters) containing the carbon sources of any one of A to F and X (reference example) as mentioned below and other components of $KH_2PO_4$ (7 g), $MgSO_4.7H_2O$ (2.5 g), NaCl (0.1 g), yeast extract (3 g) and water (1 liter). To each medium was inoculated a pure culture of Torulopsis sp. ATCC 20507 (FERM-P No. 3904), and each was cultivated under the conditions of aeration volume: 1 V.V.M., rate of stirring: 300 r.p.m., cultivation temperature: 35° C. and cultivation time: 28 hours.

Carbon source in the medium:
(A): Methyl stearate (18 g) and methyl palmitate (2 g)
(B): Ethyl stearate (13 g) and butyl palmitate (7 g)
(C): Stearyl alcohol (17 g) and methyl palmitate (3 g)
(D): Vinyl stearate (13 g) and vinyl palmitate (7 g)
(E): Methyl stearate (9 g), methyl palmitate (4 g) and oleic acid (7 g)
(F): Stearyl chloride (18 g) and palmityl acetate (2 g)
(X) (Reference Example): Methyl stearate (20 g)

After the cultivation, the cells were collected and the fats and oils were recovered therefrom and the characteristics thereof were measured in the same manner as described in Example 1. The results are shown in Table 2.

As is clear from the results, when the microorganism was cultivated in the medium containing the carbon sources A to F of the present invention, there was obtained the desired fats and oils having a high SUS content, but on the other hand, when the microorganism was cultivated in the medium containing the carbon source X (methyl stearate alone) of Reference Example, the yield of the cells and the yield of the fats and oils as well as the SUS content were lower.

TABLE 2

| | Carbon source in the medium | | | | | | |
|---|---|---|---|---|---|---|---|
| | A | B | C | D | E | F | X |
| Yield of cells (kg) | 0.94 | 1.10 | 0.92 | 1.23 | 1.30 | 0.88 | 0.48 |
| Yield of fats and oils (kg) | 0.48 | 0.55 | 0.32 | 0.63 | 0.68 | 0.30 | 0.25 |
| Content of fats and oils in cells (%) | 51.5 | 50.3 | 34.8 | 51.2 | 52.3 | 34.1 | 52.8 |
| Yield of fats and oils (per consumed carbon source) (%) | 38.8 | 38.9 | 23.7 | 33.2 | 35.0 | 21.1 | 18.7 |
| Iodine value | 54.3 | 44.2 | 30.3 | 37.4 | 52.4 | 50.9 | 52.9 |
| Acid value | 2.0 | 5.5 | 6.1 | 1.0 | 8.0 | 3.7 | 4.2 |
| Fatty acids components (%) | | | | | | | |
| $C_{14:0}$ | — | 0.4 | 0.2 | 0.5 | 0.3 | 0.4 | 0.3 |
| $C_{16:0}$ | 6.6 | 26.0 | 10.4 | 26.0 | 19.0 | 19.5 | 4.2 |
| $C_{16:0}-C_{18:0}$ | 2.0 | 3.4 | 1.0 | 6.3 | 3.2 | 4.6 | 2.6 |
| $C_{18:0}$ | 35.6 | 26.3 | 56.6 | 37.0 | 28.1 | 26.5 | 40.2 |
| $C_{18:1}$ | 51.7 | 41.1 | 29.5 | 21.9 | 41.8 | 44.0 | 47.9 |
| $C_{18:2}$ | 3.9 | 2.8 | 1.7 | 8.0 | 7.3 | 4.9 | 4.8 |
| $C_{18:3}$ | — | — | 0.2 | 0.1 | 0.1 | — | — |
| $C_{20:0}$ | 0.2 | — | 0.3 | 0.2 | 0.2 | 0.1 | — |
| Triglycerides arrangement (%) | | | | | | | |
| Tri-saturat. glycerides | 3.9 | 11.2 | 21.4 | 19.4 | 5.7 | 8.2 | 6.8 |
| Di-saturat. glycerides | | | | | | | |
| 2-saturated | 5.2 | 9.0 | 6.2 | 8.6 | 5.5 | 9.8 | 9.1 |
| 2-unsaturated | 31.5 | 40.0 | 55.0 | 47.5 | 39.5 | 30.8 | 28.8 |
| Di-unsaturat. glycerides | | | | | | | |
| 2-saturated | 1.8 | 1.8 | 0.4 | 1.0 | 1.3 | 3.0 | 3.1 |
| 2-unsaturated | 43.0 | 31.7 | 15.9 | 21.1 | 38.6 | 37.0 | 39.0 |
| Tri-unsaturat. glycerides | 14.6 | 6.3 | 1.1 | 2.4 | 9.4 | 11.2 | 13.2 |

EXAMPLE 3

A 150 liter fermentor provided with a stirrer and aeration duct was charged with a medium (pH 4.5, 100 liters) containing methyl stearate (14 g), methyl palmitate (6 g), $KH_2PO_4$ (1 g), $MgSO_4.7H_2O$ (0.5 g), NaCl (1 g), yeast extract (3 g), $CaCl_2.2H_2O$ (0.5 g), vitamin $B_1$ (300 μg), $FeCl_3.6H_2O$ (2 mg), $ZnSO_4.7H_2O$ (2 mg) and water (1 liter), and thereto was inoculated a pure culture (2 liters) of Torulopsis sp. ATCC 20507 (FERM-P No. 3904) and it was cultivated under the conditions of aeration volume: 1 V.V.M., rate of stirring: 800 r.p.m., cultivation temperature: 35° C. and cultivation time: 28 hours. After the cultivation, the cells were collected with a nozzle separator type centrifugal machine, lyophilized and weighed (yield of the cells: 1115 g). Crude fats and oils (550 g) were recovered from the cells and the characteristics of the crude fats and oils thus obtained were measured in the same manner as described in Example 1. The results are shown in Table 3.

The crude fats and oils (200 g) obtained above were deacidated in a usual manner and thereafter were dissolved in n-hexane (300 g). The solution was stirred at −15° C. for one hour, and the precipitated crystals (fraction having medium and high melting points) were collected by filtration. The resulting filtrate was further stirred at 11° C. for an additional one hour and filtered to separate into the precipitated crystals (fraction having a high melting point) and a liquid fraction (fraction having a medium melting point). Each fraction was distilled to remove h-hexane and weighed. The yield of fractions was each 10.2% by weight (the high melting point fraction), 53.9% (the medium melting point fraction) and 35.9% by weight (the low melting point fraction), respectively. The characteristics of this medium melting point fraction were measured, likewise. The results are also shown in Table 3.

TABLE 3

| | Crude fats and oils | Medium melting point fraction |
|---|---|---|
| Iodine value | 46.3 | 40.6 |
| Acid value | 4.5 | — |
| Saponification value | 189.7 | — |
| Fatty acids components (%) | | |
| $C_{14:0}$ | 0.1 | 0.2 |
| $C_{16:0}$ | 18.3 | 20.2 |
| $C_{16:0}-C_{18:0}$ | 2.2 | 2.0 |
| $C_{18:0}$ | 32.2 | 36.5 |
| $C_{18:1}$ | 43.0 | 38.5 |
| $C_{18:2}$ | 3.6 | 2.0 |
| $C_{18:3}$ | 0.2 | — |
| $C_{20:0}$ | 0.3 | 0.6 |
| Triglycerides arrangement (%) | | |
| Tri-saturat. glycerides | 6.1 | 4.2 |
| Di-saturat. glycerides | | |
| 2-saturated | 4.9 | 1.8 |
| 2-unsaturated | 44.9 | 63.2 |
| Di-unsaturat. glycerides | | |
| 2-saturated | 1.0 | 0.2 |
| 2-unsaturated | 35.9 | 27.6 |
| Tri-unsaturat. glycerides | 7.2 | 3.0 |

Besides, the cooling curve of the fats and oils of the medium melting point fraction and also that of cacao butter (reference) were measured. The results are shown in the accompanying FIGURE, wherein the curve 1 is the cooling curve of the medium melting point fraction and the curve 2 is that of cacao butter.

What is claimed is:

1. In a method for producing fats and oils rich in 1,3-disaturated-2-unsaturated-triglycerides useful as a cacao butter substitute, comprising cultivating a microorganism being capable of assimilating a higher alkyl derivative and producing fats and oils containing 1,3-disaturated-2-unsaturated-triglycerides in a medium under an aerobic condition, collecting the cells of the microorganism and recovering the fats and oils from the cells, the improvement wherein the medium contains a mixed carbon source comprising at least one stearyl compound selected from the group consisting of an alkyl stearate having 1 to 4 carbon atoms in the alkyl moiety, vinyl stearate, stearyl acetate, stearyl alcohol, stearyl chloride and ammonium stearate, and at least one other carbon compound selected from the group consisting of a palmityl compound, an oleyl compound and a saccharide.

2. The method according to claim 1, wherein the alkyl stearate is a member selected from the group consisting of methyl stearate, ethyl stearate and n-butyl stearate.

3. The method according to claim 1, wherein the stearyl compound is contained in the medium in an amount of 10 to 95% by weight based on the total weight of the carbon sources.

4. The method according to claim 3, wherein the content of the stearyl compound is in the range of 25 to 85% by weight based on the total weight of the carbon sources.

5. The method according to claim 1, wherein the palmityl compound is a member selected from the group consisting of methyl palmitate, ethyl palmitate, butyl palmitate, vinyl palmitate, palmityl acetate, palmityl alcohol and palmityl chloride.

6. The method according to claim 1, wherein the oleyl compound is a member selected from the group consisting of oleic acid, methyl oleate, ethyl oleate, butyl oleate, vinyl oleate, oleyl acetate, oleyl alcohol and oleyl chloride.

7. The method according to claim 1, wherein the saccharide is a member selected from the group consisting of a monosaccharide, an oligosaccharide and a water-soluble polysaccharide.

8. The method according to claim 1, wherein the microorganism is a microorganism being capable of assimilating the stearyl compound, palmityl compound and oleyl compound.

9. The method according to claim 1, wherein the microorganism is a member selected from the group consisting of the microorganisms of the genus Candida, Torulopsis, Trichosporon, Pichia and Sporobolomyces.

* * * * *